US 6,696,397 B2

United States Patent
Staats

(10) Patent No.: US 6,696,397 B2
(45) Date of Patent: Feb. 24, 2004

(54) ANTIBACTERIAL SOAP

(76) Inventor: Victor Staats, P.O. Box 616, Marble, NC (US) 28905

( * ) Notice: Subject to any disclaimer, the term of this patent is extended or adjusted under 35 U.S.C. 154(b) by 0 days.

(21) Appl. No.: 10/413,604

(22) Filed: Apr. 14, 2003

(65) Prior Publication Data

US 2003/0203824 A1 Oct. 30, 2003

Related U.S. Application Data

(60) Provisional application No. 60/376,785, filed on Apr. 30, 2002.

(51) Int. Cl.⁷ .............................. C11D 17/00; A61K 7/50
(52) U.S. Cl. .................. 510/130; 510/161; 510/424; 510/426; 510/463; 510/459; 510/505
(58) Field of Search .................................. 510/119, 125, 510/130, 424, 426, 505, 499, 463, 137, 138, 161

(56) References Cited

U.S. PATENT DOCUMENTS

| 6,214,363 | B1 | * | 4/2001 | Beerse et al. ................ 424/404 |
| 6,265,363 | B1 | * | 7/2001 | Viscovitz et al. ............ 510/130 |
| 6,281,189 | B1 | * | 8/2001 | Heimann et al. ............ 510/491 |
| 6,376,437 | B2 | * | 4/2002 | Viscovitz et al. ............ 510/130 |
| 2002/0013237 | A1 | * | 1/2002 | Viscovitz et al. ............ 510/130 |

* cited by examiner

*Primary Examiner*—Necholus Ogden
(74) *Attorney, Agent, or Firm*—Robert M. Downey, PA

(57) ABSTRACT

An antiseptic soap composition includes alcohol as an active ingredient in combination with a sudsing agent. In a preferred embodiment, the composition includes: SD 40 alcohol or isopropyl alcohol in an amount of between 35% and 80% by weight; ammonium lauryl sulfate as a sudsing agent in an amount of between 5% and 30% by weight; one or more oils as a grease cutting agent and fragrance enhancer; one or more thickening agents; a catalyst; and water.

7 Claims, No Drawings

ANTIBACTERIAL SOAP

This application claims the benefit of priority to U.S. Provisional Patent Application Serial No. 60/346,785, filed Apr. 30, 2002, the entirety of which is incorportated herein by reference.

BACKGROUND OF THE INVENTION

1. Field of the Invention

The present invention relates to a sudsy antiseptic soap and, more particularly, to a composition for an antiseptic soap including alcohol as an active ingredient in combination with a sudsing agent to provide a long-lasting germicidal sudsing soap which cuts through grease, grime and dirt.

2. Discussion of the Related Art

The prior art is crowded with antiseptic soap products, many of which are intended for clinical and domestic use. In testing, it has been found that many antiseptic soap products on the market today do not provide an efficacy which meets the high standards of the medical and food preparation industries. While various antimicrobial agents are known to provide sufficient efficacy, they lack the grease, blood and dirt cutting action needed to remove debris and sufficiently cleanse the surface of the skin and various articles, such as medical instruments and utensils. While a sudsy iodine product exists on the market, it is not environmentally friendly and is generally not desirable for use in either a clinical environment or domestic environment.

SUMMARY OF THE INVENTION

The present invention is directed to a highly effective antiseptic soap which is ideal for use in both medical environments as well as households. The antiseptic soap composition of the present invention uses alcohol as the active ingredient in a long-lasting soap matrix. In a preferred embodiment, the composition includes: SD 40 alcohol or isopropyl alcohol in an amount of between 35% and 80% by weight of the composition; ammonium lauryl sulfate as a sudsing agent in an amount of between 5% and 30% by weight of the composition; one or more oils as a grease cutting agent and fragrance enhancer; one or more co-polymers for thickening; other thickening and spreading agents; a catalyst; and water. The composition of the present invention provides:

- a long-lasting antiseptic soap to remove dirt, grease and grime from the hands and skin;
- clinicians with a one-step grease, dirt and blood cleansing antimicrobial matrix;
- clinicians, consumers and the environment with a germicide that does not cause collateral damage;
- clinicians with a one-step product to clean and disinfect medical instruments;
- consumers with a one-step product to clean and disinfect toys, eating utensils and areas where dirt, grime and harmful pathogens must be removed;
- a long-lasting soap to remove dirt, grime, human and environmental debris from the hands and skin;
- a one-step antimicrobial cleansing agent for human and animals which is safe and environmentally friendly;
- alcohol in a long-lasting soap with desensitizing cleansing action which cleans wounds while maintaining the high standards of the medical and food preparation industries.

DETAILED DESCRIPTION OF THE PREFERRED EMBODIMENTS

The present invention is directed to a long lasting, high suds producing germicidal soap which effectively cuts dirt, grease and grime and, more particularly, to a one-step sudsy antiseptic soap composition.

The antiseptic soap composition of the present invention incorporates the use of an alcohol as the active antimicrobial and germicidal ingredient and is present in amounts of 35% by weight or greater. In a preferred embodiment, the alcohol active ingredient is SD 40 alcohol or isopropyl alcohol present in the composition in an amount of between 35% and 80% by weight of the composition.

The antiseptic soap composition of the present invention further incorporates a sudsing agent. In a preferred embodiment, the sudsing agent is present in the composition in an amount of between 5% and 35% by weight of the composition. While various sudsing agents are contemplated, ammonium lauryl sulfate and sodium lauryl sulfate are preferred sudsing agents according to a best mode of the invention at this time. The sudsing agent assists with cleansing by cutting grease, grime and dirt from skin and other surfaces.

One or more oils are used to aid in cutting grease and to assist in the sudsing cleansing action of the soap composition. A broad spectrum of oils are suitable for use as the grease cutting agent, including petroleum based oils, animal based oils and vegetable based oils. In the preferred embodiment, vegetable oils are used. Specifically, corn oil and D-Limonene are preferred, due to their nontoxic nature and suitability for cosmetic products. Corn oil is particularly favorable for the skin, leaving the skin soft, smooth and with a vibrant feel. D-Limonene is favorable due to its pleasant natural fragrance. In a preferred embodiment, the one or more oils are present in an amount of between 0.05% and 5% by weight of the composition.

The composition further includes at least one thickening agent. In a preferred embodiment, a copolymer is provided for thickening alone or in combination with other thickening agents. The preferred embodiment incorporates the use of copolymer 940 for thickening of the composition. The copolymer is present in the amount of between 0.02% and 5.0% by weight of the composition.

Other contemplated thickening agents include lapinite and/or cellulose. These and other contemplated thickening agents are present in an amount of between 0.01% and 5.0% by weight of the composition.

Triethanolamine is used as a catalyst for the copolymer. In a preferred embodiment, the catalyst is present in an amount of between 0.001% and 4.0% by weight of the composition.

When used in clinical environments, the composition may further be provided with one or more components for removing blood from the surface of skin and medical instruments. In a preferred embodiment, the composition incorporates disodium EDTA in an amount of between 0.05% and 1.0% by weight of the composition. Alternatively, tetrasodium EDTA may be used as a blood-removing agent, particularly for skin. In a preferred embodiment, tetrasodium EDTA is present in an amount of between 0.005% and 0.10% by weight of the composition.

LIDOCAINE may be used in the composition for desensitizing purposes. The use of a desensitizing component in the composition is particularly useful for first aid products, such as wound cleansers.

The following examples demonstrate various combinations of ingredients for different products contemplated within the spirit and scope of the invention, all of which incorporate the essential ingredients, including alcohol, a sudsing agent and a thickening agent.

EXAMPLE 1

MEDICAL INSTRUMENT CLEANING PRODUCT

| Ingredient | Amount (% by Weight of the Composition) |
| --- | --- |
| SD 40 alcohol | 70% |
| Ammonium lauryl sulfate | 15% |
| Disodium EDTA | 0.2% |
| Copolymer 940 | 0.02% |
| Lapinite | 0.01% |
| Triethanolamine | 0.01% |
| De-ionized water | To 100% of the composition |

EXAMPLE 2

HAND SOAP PRODUCT

| Ingredient | Amount (% by Weight of the Composition) |
| --- | --- |
| Isopropyl alcohol | 62% |
| Sodium lauryl sulfate | 12% |
| Hydrolyzed callogen | 0.05% |
| Tetrasodium EDTA | 0.05% |
| Copolymer 940 | 0.01% |
| Cellulose | 0.02% |
| Triethanolamine | 0.01% |
| De-ionized water | To 100% of the composition |

*Pumice may be added as an exfoliate.

EXAMPLE 3

HAND SOAP PRODUCT

| Ingredient | Amount (% by Weight of the Composition) |
| --- | --- |
| Isopropyl alcohol | 60% |
| Sodium lauryl sulfate | 11% |
| Corn Oil | 1.5% |
| D-Limonene | 0.5% |
| Hydrolyzed callogen | 0.05% |
| Tetrasodium EDTA | 0.05% |
| Copolymer 940 | 0.01% |
| Cellulose | 0.02% |
| Triethanolamine | 0.01% |
| De-ionized water | To 100% of the composition |

*Pumice may be added as an exfoliate.

EXAMPLE 4

WOUND CLEANSER

| Ingredient | Amount (% by Weight of the Composition) |
| --- | --- |
| SD 40 alcohol | 65% |
| Sodium lauryl sulfate | 12% |
| Disodium EDTA | 0.2% |
| Copolymer 940 | 0.02% |

EXAMPLE 4-continued

WOUND CLEANSER

| Ingredient | Amount (% by Weight of the Composition) |
| --- | --- |
| Lapinite | 0.02% |
| LIDOCAINE | 2.5% |
| Triethanolamine | 0.01% |
| De-ionized water | To 100% of the composition |

While the instant invention has been described in accordance with preferred and practical embodiments thereof, it is recognized that departures from the instant disclosure are contemplated within the spirit and scope of the present invention.

What is claimed is:

1. An antiseptic soap composition comprising:
   an alcohol in an amount of between 35% and 80% by weight of the composition selected from the group consisting of SD 40 alcohol and isopropyl alcohol;
   a sudsing agent in an amount of between 5% and 35% by weight of the composition selected from the group consisting of ammonium lauryl sulfate and sodium lauryl sulfate;
   a thickening agent in an amount of between 0.2% and 5.0% by weight of the composition;
   a catalyst in an amount of between 0.001% and 4.0% by weight of the composition; and
   water.

2. The composition as recited in claim 1 wherein said thickening agent is a copolymer.

3. The composition as recited in claim 1 wherein said catalyst is Triethanolamine.

4. The composition as recited in claim 1 further comprising at least one oil as a grease-cutting agent.

5. The composition as recited in claim in claim 4 wherein said at least one oil includes corn oil.

6. The composition as recited in claim 4 wherein said at least one oil includes D-Limonene.

7. An antiseptic soap composition comprising:
   an alcohol in an amount of between 35% and 80% by weight of the composition selected from the group consisting of SD 40 alcohol and isopropyl alcohol;
   a sudsing agent in an amount of between 5% and 35% by weight of the composition selected from the group consisting of ammonium lauryl sulfate and sodium lauryl sulfate;
   at least one oil as a grease-cutting agent in an amount of between 0.05% and 5.0% by weight of the composition;
   a thickening agent in an amount of between 0.2% and 5.0% by weight of the composition;
   a catalyst in an amount of between 0.001% and 4.0% by weight of the composition; and
   water.

\* \* \* \* \*